(12) United States Patent
Andrews

(10) Patent No.: US 7,811,403 B2
(45) Date of Patent: *Oct. 12, 2010

(54) TRANSVERSE TAB APPLICATION METHOD AND APPARATUS

(75) Inventor: Robert E. Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 369 days.

This patent is subject to a terminal disclaimer.

(21) Appl. No.: 11/800,627

(22) Filed: May 7, 2007

(65) Prior Publication Data

US 2007/0256777 A1 Nov. 8, 2007

Related U.S. Application Data

(63) Continuation-in-part of application No. 11/371,468, filed on Mar. 9, 2006, now Pat. No. 7,452,436.

(60) Provisional application No. 60/659,785, filed on Mar. 9, 2005.

(51) Int. Cl.
| | |
|---|---|
| *B29C 65/50* | (2006.01) |
| *B29C 65/56* | (2006.01) |
| *B32B 37/22* | (2006.01) |
| *B44C 1/24* | (2006.01) |
| *B65C 9/30* | (2006.01) |
| *B32B 37/26* | (2006.01) |
| *B44C 1/17* | (2006.01) |
| *B65C 9/20* | (2006.01) |

(52) U.S. Cl. .................. 156/249; 156/238; 156/247; 156/469; 156/519; 156/571

(58) Field of Classification Search .................. 156/230, 156/238, 241, 247, 249, 312, 465, 469, 517, 156/519, 521, 571
See application file for complete search history.

(56) References Cited

U.S. PATENT DOCUMENTS

| 135,145 A | 1/1873 | Murphy |
|---|---|---|
| 293,353 A | 2/1884 | Purvis |
| 312,257 A | 2/1885 | Cotton et al. |
| 410,123 A | 8/1889 | Stilwell |

(Continued)

FOREIGN PATENT DOCUMENTS

BE 1007854 11/1995

(Continued)

OTHER PUBLICATIONS

Reciprocating Mechanisms, Ingenious Mechanisms for Designers and Inventors, Franklin Jones vol. 1.

(Continued)

*Primary Examiner*—Philip C Tucker
*Assistant Examiner*—Sonya Mazumdar
(74) *Attorney, Agent, or Firm*—Ryan Kromholz & Manion, S.C.

(57) ABSTRACT

A method and apparatus for applying tabs to a traveling web of material at a transfer position when the tabs are provided to the transfer position in a path that is skew to the web travel path. A tab supply assembly carries the tabs in a tab path that is either perpendicularly skew or obliquely skew to the travel path of the web. The web is generally spaced from the tab supply assembly. A plurality of bump transfer surfaces is adapted to urge the web towards the tab supply assembly, thereby contacting a tab.

15 Claims, 7 Drawing Sheets

U.S. PATENT DOCUMENTS

| | | | |
|---|---|---|---|
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |
| 2,282,477 A | 5/1942 | Joa | |
| 2,286,096 A | 6/1942 | Joa | |
| 2,296,931 A | 9/1942 | Joa | |
| 2,304,571 A | 12/1942 | Joa | |
| 2,324,930 A | 7/1943 | Joa | |
| 2,345,937 A | 4/1944 | Joa | |
| 2,466,240 A | 4/1949 | Joa | |
| 2,481,929 A | 9/1949 | Joa | |
| 2,510,229 A | 6/1950 | Joa | |
| 2,540,844 A | 2/1951 | Strauss | |
| 2,584,002 A | 1/1952 | Elser et al. | |
| 2,591,359 A | 4/1952 | Joa | |
| 2,618,816 A | 11/1952 | Joa | |
| 2,702,406 A | 2/1955 | Reed | |
| 2,721,554 A | 10/1955 | Joa | |
| 2,730,144 A | 1/1956 | Joa | |
| 2,772,611 A | 12/1956 | Heywood | |
| 2,780,253 A | 2/1957 | Joa | |
| 2,785,609 A | 3/1957 | Billeb | |
| 2,811,905 A | 11/1957 | Kennedy, Jr | |
| 2,839,059 A | 6/1958 | Joa | |
| 2,842,169 A | 7/1958 | Joa | |
| 2,851,934 A | 9/1958 | Heywood | |
| 2,875,724 A | 3/1959 | Joa | |
| 2,913,862 A | 11/1959 | Sabee | |
| 2,939,461 A | 6/1960 | Joa | |
| 2,939,646 A | 6/1960 | Stone | |
| 2,960,143 A | 11/1960 | Joa | |
| 2,990,081 A | 6/1961 | Neui et al. | |
| 2,991,739 A | 7/1961 | Joa | |
| 3,016,207 A | 1/1962 | Comstock | |
| 3,016,582 A | 1/1962 | Joa | |
| 3,017,795 A | 1/1962 | Joa | |
| 3,020,687 A | 2/1962 | Joa | |
| 3,021,135 A | 2/1962 | Joa | |
| 3,024,957 A | 3/1962 | Pinto | |
| 3,053,427 A | 9/1962 | Wasserman | |
| 3,054,516 A | 9/1962 | Joa | |
| 3,069,982 A | 12/1962 | Heywood et al. | |
| 3,086,253 A | 4/1963 | Joa | |
| 3,087,689 A | 4/1963 | Heim | |
| 3,091,408 A | 5/1963 | Schoeneman | |
| 3,114,994 A | 12/1963 | Joa | |
| 3,122,293 A | 2/1964 | Joa | |
| 3,128,206 A | 4/1964 | Dungler | |
| 3,203,419 A | 8/1965 | Joa | |
| 3,230,955 A | 1/1966 | Joa et al. | |
| 3,268,954 A | 8/1966 | Joa | |
| 3,288,037 A | 11/1966 | Burnett | |
| 3,289,254 A | 12/1966 | Joa | |
| 3,291,131 A | 12/1966 | Joa | |
| 3,301,114 A | 1/1967 | Joa | |
| 3,322,589 A | 5/1967 | Joa | |
| 3,342,184 A | 9/1967 | Joa | |
| 3,356,092 A | 12/1967 | Joa | |
| 3,360,103 A | 12/1967 | Johnson | |
| 3,363,847 A | 1/1968 | Joa | |
| 3,391,777 A | 7/1968 | Joa | |
| 3,454,442 A | 7/1969 | Heller, Jr. | |
| 3,463,413 A | 8/1969 | Smith | |
| 3,470,848 A | 10/1969 | Dreher | |
| 3,484,275 A | 12/1969 | Lewicki, Jr. | |
| 3,502,322 A | 3/1970 | Cran | |
| 3,521,639 A | 7/1970 | Joa | |
| 3,526,563 A | 9/1970 | Schott, Jr. | |
| 3,538,551 A | 11/1970 | Joa | |
| 3,540,641 A | 11/1970 | Besnyo et al. | |
| 3,575,170 A | 4/1971 | Clark | |
| 3,607,578 A * | 9/1971 | Berg et al. | 156/552 |
| 3,635,462 A | 1/1972 | Joa | |
| 3,656,741 A | 4/1972 | Macke et al. | |
| 3,666,611 A | 5/1972 | Joa | |
| 3,673,021 A | 6/1972 | Joa | |
| 3,685,818 A | 8/1972 | Burger | |
| 3,728,191 A | 4/1973 | Wierzba et al. | |
| 3,751,224 A | 8/1973 | Wackerle | |
| 3,758,102 A | 9/1973 | Munn et al. | |
| 3,772,120 A | 11/1973 | Radzins | |
| 3,776,798 A | 12/1973 | Milano | |
| 3,796,360 A | 3/1974 | Alexeff | |
| 3,811,987 A | 5/1974 | Wilkinson et al. | |
| 3,816,210 A | 6/1974 | Aoko et al. | |
| 3,847,710 A * | 11/1974 | Blomqvist et al. | 156/511 |
| 3,854,917 A | 12/1974 | McKinney et al. | |
| 3,883,389 A | 5/1975 | Schott, Jr. | |
| 3,888,400 A | 6/1975 | Wiig | |
| 3,901,238 A | 8/1975 | Gellert et al. | |
| 3,903,768 A | 9/1975 | Amberg et al. | |
| 3,904,147 A | 9/1975 | Taitel et al. | |
| 3,918,698 A | 11/1975 | Coast | |
| 3,960,646 A | 6/1976 | Wiedamann | |
| 3,988,194 A | 10/1976 | Babcock et al. | |
| 3,991,994 A | 11/1976 | Farish | |
| 4,002,005 A | 1/1977 | Mueller et al. | |
| 4,003,298 A | 1/1977 | Schott, Jr. | |
| 4,009,814 A | 3/1977 | Singh | |
| 4,009,815 A | 3/1977 | Ericson et al. | |
| 4,053,150 A | 10/1977 | Lane | |
| 4,056,919 A | 11/1977 | Hirsch | |
| 4,081,301 A | 3/1978 | Buell | |
| 4,090,516 A | 5/1978 | Schaar | |
| 4,094,319 A | 6/1978 | Joa | |
| 4,103,595 A | 8/1978 | Corse | |
| 4,106,974 A | 8/1978 | Hirsch | |
| 4,108,584 A | 8/1978 | Radzins et al. | |
| 4,136,535 A | 1/1979 | Audas | |
| 4,141,193 A | 2/1979 | Joa | |
| 4,141,509 A | 2/1979 | Radzins | |
| 4,142,626 A | 3/1979 | Bradley | |
| 4,157,934 A | 6/1979 | Ryan et al. | |
| 4,165,666 A | 8/1979 | Johnson et al. | |
| 4,168,776 A | 9/1979 | Hoeboer | |
| 4,171,239 A | 10/1979 | Hirsch et al. | |
| 4,205,679 A | 6/1980 | Repke et al. | |
| 4,208,230 A | 6/1980 | Magarian | |
| 4,213,356 A | 7/1980 | Armitage | |
| 4,215,827 A | 8/1980 | Roberts et al. | |
| 4,222,533 A | 9/1980 | Pongracz | |
| 4,223,822 A | 9/1980 | Clitheroe | |
| 4,231,129 A | 11/1980 | Winch | |
| 4,236,955 A | 12/1980 | Prittie | |
| 4,275,510 A | 6/1981 | George | |
| 4,284,454 A | 8/1981 | Joa | |
| 4,307,800 A | 12/1981 | Joa | |
| 4,316,756 A * | 2/1982 | Wilson | 156/227 |
| 4,325,519 A | 4/1982 | McLean | |
| 4,342,206 A | 8/1982 | Rommel | |

| | | | | | | |
|---|---|---|---|---|---|---|
| 4,364,787 A | 12/1982 | Radzins | | 5,127,981 A | 7/1992 | Straub et al. |
| 4,374,576 A | 2/1983 | Ryan | | 5,131,525 A | 7/1992 | Musschoot |
| 4,379,008 A | 4/1983 | Gross et al. | | 5,133,511 A | 7/1992 | Mack et al. |
| 4,394,898 A | 7/1983 | Campbell | | 5,147,487 A | 9/1992 | Nomura et al. |
| 4,411,721 A | 10/1983 | Wishart | | 5,163,594 A | 11/1992 | Meyer |
| 4,452,597 A | 6/1984 | Achelpohl | | 5,171,239 A | 12/1992 | Igaue et al. |
| 4,492,608 A | 1/1985 | Hirsch et al. | | 5,176,244 A | 1/1993 | Radzins et al. |
| 4,501,098 A | 2/1985 | Gregory | | 5,183,252 A | 2/1993 | Wolber et al. |
| 4,508,528 A | 4/1985 | Hirsch et al. | | 5,188,627 A | 2/1993 | Igaue et al. |
| 4,522,853 A | 6/1985 | Szonn et al. | | 5,190,234 A | 3/1993 | Ezekiel |
| 4,543,152 A | 9/1985 | Nozaka | | 5,195,684 A | 3/1993 | Radzins |
| 4,551,191 A | 11/1985 | Kock et al. | | 5,203,043 A | 4/1993 | Riedel |
| 4,586,199 A | 5/1986 | Birring | | 5,213,645 A | 5/1993 | Nomura et al. |
| 4,589,945 A | 5/1986 | Polit | | 5,222,422 A | 6/1993 | Benner, Jr. et al. |
| 4,603,800 A | 8/1986 | Focke et al. | | 5,223,069 A | 6/1993 | Tokuno et al. |
| 4,614,076 A | 9/1986 | Rathemacher | | 5,226,992 A | 7/1993 | Morman |
| 4,619,357 A | 10/1986 | Radzins et al. | | 5,246,433 A | 9/1993 | Hasse et al. |
| 4,634,482 A | 1/1987 | Lammers | | 5,252,228 A | 10/1993 | Schaupp |
| 4,641,381 A | 2/1987 | Heran et al. | | 5,267,933 A | 12/1993 | Precoma |
| 4,642,150 A | 2/1987 | Stemmler | | 5,273,228 A | 12/1993 | Yoshida et al. |
| 4,642,839 A | 2/1987 | Urban | | 5,308,345 A | 5/1994 | Herrin |
| 4,650,530 A | 3/1987 | Mahoney et al. | | 5,328,438 A | 7/1994 | Crowley |
| 4,663,220 A | 5/1987 | Wisneski et al. | | 5,340,424 A | 8/1994 | Matsushita |
| 4,672,705 A | 6/1987 | Bors et al. | | 5,368,893 A | 11/1994 | Sommer et al. |
| 4,675,062 A | 6/1987 | Instance | | 5,407,513 A | 4/1995 | Hayden et al. |
| 4,693,056 A | 9/1987 | Raszewski | | 5,415,649 A | 5/1995 | Watanabe et al. |
| 4,701,239 A * | 10/1987 | Craig .................. 156/519 | | 5,421,924 A | 6/1995 | Ziegelhoffer et al. |
| 4,723,698 A | 2/1988 | Schoonderbeek | | 5,424,025 A | 6/1995 | Hanschen et al. |
| 4,726,874 A | 2/1988 | Van Vliet | | 5,429,576 A * | 7/1995 | Doderer-Winkler ......... 493/214 |
| 4,726,876 A | 2/1988 | Tomsovic et al. | | 5,435,802 A | 7/1995 | Kober |
| 4,743,241 A | 5/1988 | Igaue et al. | | 5,449,353 A | 9/1995 | Watanabe et al. |
| 4,751,997 A | 6/1988 | Hirsch | | 5,464,401 A | 11/1995 | Hasse et al. |
| 4,753,429 A | 6/1988 | Irvine et al. | | 5,486,253 A | 1/1996 | Otruba |
| 4,756,141 A | 7/1988 | Hirsch et al. | | 5,494,622 A | 2/1996 | Heath et al. |
| 4,764,325 A | 8/1988 | Angstadt | | 5,531,850 A | 7/1996 | Herrmann |
| 4,765,780 A | 8/1988 | Angstadt | | 5,540,647 A | 7/1996 | Weiermann et al. |
| 4,776,920 A | 10/1988 | Ryan | | 5,545,275 A | 8/1996 | Herrin et al. |
| 4,777,513 A | 10/1988 | Nelson | | 5,545,285 A | 8/1996 | Johnson |
| 4,782,647 A | 11/1988 | Williams et al. | | 5,552,013 A | 9/1996 | Ehlert et al. |
| 4,785,986 A | 11/1988 | Daane et al. | | 5,556,360 A | 9/1996 | Kober et al. |
| 4,795,510 A | 1/1989 | Wittrock et al. | | 5,556,504 A | 9/1996 | Rajala et al. |
| 4,798,353 A | 1/1989 | Peugh | | 5,560,793 A | 10/1996 | Ruscher et al. |
| 4,801,345 A | 1/1989 | Dussaud et al. | | 5,602,747 A | 2/1997 | Rajala |
| 4,802,570 A | 2/1989 | Hirsch et al. | | 5,603,794 A | 2/1997 | Thomas |
| 4,840,609 A | 6/1989 | Jones et al. | | 5,624,420 A | 4/1997 | Bridges et al. |
| 4,845,964 A | 7/1989 | Bors et al. | | 5,624,428 A | 4/1997 | Sauer |
| 4,864,802 A | 9/1989 | D'Angelo | | 5,628,738 A | 5/1997 | Suekane |
| 4,880,102 A | 11/1989 | Indrebo | | 5,634,917 A | 6/1997 | Fujioka et al. |
| 4,888,231 A | 12/1989 | Angstadt | | 5,643,165 A | 7/1997 | Klekamp |
| 4,892,536 A | 1/1990 | DesMarais et al. | | 5,643,396 A | 7/1997 | Rajala et al. |
| 4,904,440 A | 2/1990 | Angstadt | | 5,645,543 A | 7/1997 | Nomura et al. |
| 4,908,175 A | 3/1990 | Angstadt | | 5,659,229 A | 8/1997 | Rajala |
| 4,909,019 A | 3/1990 | Delacretaz et al. | | 5,660,657 A | 8/1997 | Rajala et al. |
| 4,925,520 A | 5/1990 | Beaudoin et al. | | 5,660,665 A | 8/1997 | Jalonen |
| 4,927,322 A | 5/1990 | Schweizer et al. | | 5,683,376 A | 11/1997 | Kato et al. |
| 4,927,582 A | 5/1990 | Bryson | | RE35,687 E | 12/1997 | Igaue et al. |
| 4,937,887 A | 7/1990 | Schreiner | | 5,693,165 A | 12/1997 | Schmitz |
| 4,963,072 A | 10/1990 | Miley et al. | | 5,699,653 A | 12/1997 | Hartman et al. |
| 4,987,940 A | 1/1991 | Straub et al. | | 5,707,470 A | 1/1998 | Rajala et al. |
| 4,994,010 A | 2/1991 | Doderer-Winkler | | 5,711,832 A | 1/1998 | Glaug et al. |
| 5,000,806 A | 3/1991 | Merkatoris et al. | | 5,725,518 A | 3/1998 | Coates |
| 5,021,111 A | 6/1991 | Swenson | | 5,745,922 A | 5/1998 | Rajala et al. |
| 5,025,910 A | 6/1991 | Lasure et al. | | 5,746,869 A * | 5/1998 | Hayden et al. ............... 156/265 |
| 5,045,039 A | 9/1991 | Bay | | 5,749,989 A | 5/1998 | Linman et al. |
| 5,062,597 A | 11/1991 | Martin et al. | | 5,788,797 A | 8/1998 | Herrin et al. |
| 5,064,179 A | 11/1991 | Martin | | 5,817,199 A | 10/1998 | Brennecke et al. |
| 5,064,492 A | 11/1991 | Friesch | | 5,829,164 A | 11/1998 | Kotitschke |
| 5,080,741 A | 1/1992 | Nomura et al. | | 5,836,931 A | 11/1998 | Toyoda et al. |
| 5,094,658 A | 3/1992 | Smithe et al. | | 5,858,012 A | 1/1999 | Yamaki et al. |
| 5,096,532 A | 3/1992 | Neuwirth et al. | | 5,865,393 A | 2/1999 | Kreft et al. |
| 5,108,017 A | 4/1992 | Adamski et al. | | 5,868,727 A | 2/1999 | Barr et al. |
| 5,109,767 A | 5/1992 | Nyfeler et al. | | 5,876,027 A | 3/1999 | Fukui et al. |
| 5,110,403 A | 5/1992 | Ehlert | | 5,876,792 A | 3/1999 | Caldwell |

| | | | | | | |
|---|---|---|---|---|---|---|
| 5,879,500 | A | 3/1999 | Herrin et al. | 7,066,586 B2 | 6/2006 | da Silva |
| 5,902,431 | A | 5/1999 | Wilkinson et al. | 7,077,393 B2 | 7/2006 | Ishida |
| 5,932,039 | A | 8/1999 | Popp et al. | 7,172,666 B2 | 2/2007 | Groves et al. |
| 5,938,193 | A | 8/1999 | Bluemle et al. | 7,195,684 B2 * | 3/2007 | Satoh .................. 156/163 |
| 5,964,390 | A | 10/1999 | Borresen et al. | 7,201,345 B2 | 4/2007 | Werner et al. |
| 5,964,970 | A | 10/1999 | Woolwine et al. | 7,214,174 B2 | 5/2007 | Allen et al. |
| 6,036,805 | A | 3/2000 | McNichols | 7,247,219 B2 | 7/2007 | O'Dowd |
| 6,043,836 | A | 3/2000 | Kerr et al. | 7,587,966 B2 | 9/2009 | Nakakado et al. |
| 6,050,517 | A | 4/2000 | Dobrescu et al. | 2001/0012813 A1 | 8/2001 | Bluemle |
| 6,074,110 | A | 6/2000 | Verlinden et al. | 2001/0017181 A1 * | 8/2001 | Otruba et al. .................. 156/64 |
| 6,076,442 | A | 6/2000 | Arterburn et al. | 2002/0046802 A1 | 4/2002 | Tachibana et al. |
| 6,098,249 | A | 8/2000 | Toney et al. | 2002/0059013 A1 | 5/2002 | Rajala et al. |
| 6,123,792 | A | 9/2000 | Samida et al. | 2002/0096241 A1 | 7/2002 | Instance |
| 6,171,432 | B1 | 1/2001 | Brisebois et al. | 2002/0125105 A1 | 9/2002 | Nakakado |
| 6,183,576 | B1 | 2/2001 | Couillard et al. | 2003/0000620 A1 | 1/2003 | Herrin et al. |
| 6,210,386 | B1 | 4/2001 | Inoue | 2003/0015209 A1 | 1/2003 | Gingras et al. |
| 6,212,859 | B1 | 4/2001 | Bielik, Jr. et al. | 2003/0051802 A1 | 3/2003 | Hargett |
| 6,250,048 | B1 | 6/2001 | Linkiewicz | 2003/0052148 A1 | 3/2003 | Rajala et al. |
| 6,264,784 | B1 | 7/2001 | Menard et al. | 2003/0066585 A1 | 4/2003 | McCabe |
| 6,276,421 | B1 | 8/2001 | Valenti et al. | 2003/0083638 A1 | 5/2003 | Malee |
| 6,276,587 | B1 | 8/2001 | Borresen et al. | 2003/0084984 A1 | 5/2003 | Glaug et al. |
| 6,306,122 | B1 | 10/2001 | Narawa et al. | 2003/0089447 A1 | 5/2003 | Molee et al. |
| 6,309,336 | B1 | 10/2001 | Muessig et al. | 2003/0121614 A1 | 7/2003 | Tabor |
| 6,312,420 | B1 | 11/2001 | Sasaki et al. | 2003/0135189 A1 | 7/2003 | Umebayashi |
| 6,314,333 | B1 | 11/2001 | Rajala et al. | 2004/0007328 A1 | 1/2004 | Popp et al. |
| 6,315,022 | B1 | 11/2001 | Herrin et al. | 2004/0016500 A1 | 1/2004 | Tachibana et al. |
| 6,336,921 | B1 | 1/2002 | Kato et al. | 2004/0087425 A1 | 5/2004 | Ng et al. |
| 6,358,350 | B1 | 3/2002 | Glaug et al. | 2004/0112517 A1 | 6/2004 | Groves et al. |
| 6,369,291 | B1 | 4/2002 | Uchimoto et al. | 2004/0164482 A1 | 8/2004 | Edinger |
| 6,375,769 | B1 | 4/2002 | Quereshi et al. | 2005/0000628 A1 | 1/2005 | Norrley |
| 6,391,013 | B1 | 5/2002 | Suzuki et al. | 2005/0022476 A1 | 2/2005 | Hamer et al. |
| 6,416,697 | B1 | 7/2002 | Venturino et al. | 2005/0077418 A1 | 4/2005 | Werner et al. |
| 6,431,038 | B2 | 8/2002 | Couturier | 2005/0139713 A1 | 6/2005 | Weber et al. |
| 6,443,389 | B1 | 9/2002 | Palone | 2005/0196538 A1 | 9/2005 | Sommer et al. |
| 6,446,795 | B1 | 9/2002 | Allen et al. | 2005/0230056 A1 * | 10/2005 | Meyer et al. ................ 156/517 |
| 6,473,669 | B2 | 10/2002 | Rajala et al. | 2005/0230449 A1 | 10/2005 | Meyer et al. |
| 6,475,325 | B1 | 11/2002 | Parrish et al. | 2005/0233881 A1 | 10/2005 | Meyer |
| 6,478,786 | B1 | 11/2002 | Glaug et al. | 2005/0234412 A1 | 10/2005 | Andrews et al. |
| 6,482,278 | B1 | 11/2002 | McCabe et al. | 2005/0257881 A1 | 11/2005 | Coose et al. |
| 6,494,244 | B2 | 12/2002 | Parrish et al. | 2005/0275148 A1 | 12/2005 | Beaudoin et al. |
| 6,521,320 | B2 | 2/2003 | McCabe et al. | 2006/0021300 A1 | 2/2006 | Tada et al. |
| 6,523,595 | B1 | 2/2003 | Milner et al. | 2006/0137298 A1 | 6/2006 | Oshita et al. |
| 6,524,423 | B1 | 2/2003 | Hilt et al. | 2006/0224137 A1 | 10/2006 | McCabe et al. |
| 6,547,909 | B1 | 4/2003 | Butterworth | 2006/0265867 A1 | 11/2006 | Schaap |
| 6,551,228 | B1 | 4/2003 | Richards | 2007/0074953 A1 | 4/2007 | McCabe |
| 6,551,430 | B1 | 4/2003 | Glaug et al. | 2008/0276439 A1 * | 11/2008 | Andrews et al. ............... 29/428 |
| 6,554,815 | B1 | 4/2003 | Umebayashi | 2009/0020211 A1 * | 1/2009 | Andrews et al. ............... 156/64 |
| 6,572,520 | B2 | 6/2003 | Blumle | | | |
| 6,581,517 | B1 | 6/2003 | Becker et al. | FOREIGN PATENT DOCUMENTS | | |
| 6,596,108 | B2 | 7/2003 | McCabe | | | |
| 6,605,172 | B1 | 8/2003 | Anderson et al. | CA | 1146129 | 5/1983 |
| 6,605,173 | B2 | 8/2003 | Glaug et al. | CA | 1153345 | 9/1983 |
| 6,637,583 | B1 | 10/2003 | Andersson | CA | 1190078 | 7/1985 |
| 6,648,122 | B1 | 11/2003 | Hirsch et al. | CA | 1210744 | 9/1986 |
| 6,649,010 | B2 | 11/2003 | Parrish et al. | CA | 1212132 | 9/1986 |
| 6,656,309 | B1 | 12/2003 | Parker et al. | CA | 1236056 | 5/1988 |
| 6,659,150 | B1 | 12/2003 | Perkins et al. | CA | 1249102 | 1/1989 |
| 6,659,991 | B2 | 12/2003 | Suekane | CA | 1292201 | 11/1991 |
| 6,675,552 | B2 | 1/2004 | Kunz et al. | CA | 1307244 | 9/1992 |
| 6,684,925 | B2 | 2/2004 | Nagate et al. | CA | 1308015 | 9/1992 |
| 6,722,494 | B2 | 4/2004 | Nakakado | CA | 1310342 | 11/1992 |
| 6,743,324 | B2 | 6/2004 | Hargett et al. | CA | 2023816 | 3/1994 |
| 6,758,109 | B2 | 7/2004 | Nakakado | CA | 2404154 | 10/2001 |
| 6,766,817 | B2 | 7/2004 | da Silva | CA | 2541194 | 1/2006 |
| D497,991 | S | 11/2004 | Otsubo et al. | CA | 2559517 | 5/2007 |
| 6,820,671 | B2 * | 11/2004 | Calvert ............... 156/543 | DE | 102006047280 | 4/2007 |
| 6,837,840 | B2 | 1/2005 | Yonekawa et al. | EP | 0044206 | 1/1982 |
| 6,840,616 | B2 | 1/2005 | Summers | EP | 0048011 | 3/1982 |
| 6,852,186 | B1 * | 2/2005 | Matsuda et al. ............. 156/230 | EP | 0089106 | 9/1983 |
| 6,875,202 | B2 | 4/2005 | Kumasaka et al. | EP | 0304140 | 8/1987 |
| 6,893,528 | B2 | 5/2005 | Middelstadt et al. | EP | 0439897 | 2/1990 |
| 6,918,404 | B2 | 7/2005 | Dias da Silva | EP | 0455231 | 11/1991 |
| 6,978,486 | B2 * | 12/2005 | Zhou et al. .................... 2/400 | EP | 510251 | 10/1992 |

| | | |
|---|---|---|
| EP | 0652175 | 5/1995 |
| EP | 0811473 | 12/1997 |
| EP | 0901780 | 3/1999 |
| EP | 990855 | 4/2000 |
| EP | 1132325 | 9/2001 |
| EP | 1199057 | 4/2002 |
| EP | 1272347 | 1/2003 |
| EP | 1571249 | 9/2005 |
| EP | 1619008 | 1/2006 |
| EP | 1707168 | 4/2006 |
| EP | 1726414 | 11/2006 |
| ES | 509706 | 11/1982 |
| ES | 520559 | 12/1983 |
| ES | 296211 | 12/1987 |
| FR | 2255961 | 7/1975 |
| FR | 0206208 | 12/1986 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| JP | 10035621 | 2/1982 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10-277091 | 10/1998 |
| SE | 0602047 | 5/2007 |
| WO | WO9403301 | 2/1994 |
| WO | WO9747265 | 12/1997 |
| WO | WO 199747810 | 12/1997 |
| WO | WO9821134 | 5/1998 |
| WO | WO9907319 | 2/1999 |
| WO | WO9913813 | 3/1999 |
| WO | WO9932385 | 7/1999 |
| WO | WO9965437 | 12/1999 |
| WO | WO0143682 | 6/2001 |
| WO | WO0172237 | 10/2001 |
| WO | WO4007329 | 1/2004 |
| WO | WO2005075163 | 1/2005 |

OTHER PUBLICATIONS

U.S. Appl. No. 11/110,437, Office Action, date mailed Sep. 11, 2008, Non-Final Rejection, pp. 8.

U.S. Appl. No. 11/110,437, Response to Office Action, date mailed Jan. 8, 2009, pp. 9.

U.S. Appl. No. 11/110,437, Office Action, date mailed May 4, 2009; Final Rejection, pp. 7.

U.S. Appl. No. 11/110,437, RCE—Amendment B, date mailed Aug. 4, 2009, pp. 5.

U.S. Appl. No. 11/110,437, Interview Summary, date mailed Sep. 11, 2009, pp. 3.

U.S. Appl. No. 11/110,437, Interview Summary Response, date mailed Sep. 1, 2009, pp. 3.

U.S. Appl. No. 11/371,468, Office Action; Date Mailed: Nov. 2, 2006, Non-Final Rejection, pp. 5.

U.S. Appl. No. 11/371,468, Response to Office Action-Amendment A, Date Feb. 5, 2007, pp. 3.

U.S. Appl. No. 11/371,468, Office Action, Date Mailed Nov. 2, 2006, Non-Final Rejection, pp. 5.

U.S. Appl. No. 11/371,468, Response to Office Action-Amendment B, Date Sep. 4, 2007, pp. 2.

U.S. Appl. No. 11/371,468, Date Mailed Aug. 30, 2007, pp. 3.

U.S. Appl. No. 11/371,468, Office Action, Date Mailed Nov. 14, 2007; Non-Final Rejection, pp. 8.

U.S. Appl. No. 11/371,468, Response to Office Action-Amendment C, Date May 16, 2008, pp. 4.

U.S. Appl. No. 11/371,468, Date Mailed May 19, 2008, Non-Final Rejection, pp. 2.

U.S. Appl. No. 11/371,468, Response to Interview Summary, Date Jun. 8, 2008, pp. 2.

\* cited by examiner

TRANSVERSE TAB APPLICATION METHOD AND APPARATUS

RELATED APPLICATION

This application is a continuation-in-part application of U.S. patent application Ser. No. 11/371,468, now U.S. Pat. No. 7,452,436, filed 9 Mar. 2006, and entitled "Transverse Tape Application Method and Apparatus," which claims the benefit of U.S. Provisional Patent Application Ser. No. 60/659,785, filed 9 Mar. 2005, and entitled "Transverse Tape Application Method and Apparatus."

BACKGROUND OF THE INVENTION

The present invention relates to processes and apparatus for applying tabs to traveling webs, and more specifically to a method and apparatus for applying tabs to a traveling web of material at a transfer position when the tabs are provided to the transfer position in a path that can be skew to the travel direction of the web of material. The invention has particular applicability to the manufacture of disposable diapers.

The history of cutting and applying tabs to disposable diaper webs is now entering its fourth decade. Over the course of that time, various types of automatic manufacturing equipment have been developed which produce the desired results with a variety of materials and configurations. This equipment generally included window-knife and slip-and-cut applicators, each having their own advantages and limitations.

Window-knife applicators generally comprise the following: one or more rotating heads, each made up of a knife edge and a vacuum plate; a more or less stationary knife, which is configured with a hole (window); and a tape transfer mechanism. Typically, the rotating heads are mechanically configured to eliminate head rotation relative to the stationary knife. Each head is passed, once per cycle, across the face of the stationary window knife, through which the infeeding tape is passed. The rotating knife shears the extended length of tape against the sharp inner edge of the hole (window), after which the severed segment is held by the vacuum plate. The rotating head, with the segment of tape held in place by the vacuum plate, continues through its rotation to a point, usually 90 degrees later, where it contacts the traveling web, which is pressed against the exposed adhesive of the tape segment. This contact, usually against some backing device, effects a transfer of the tape tab from the vacuum plate to the traveling web, which then carries the tape tab downstream.

Slip-and-cut applicators are typically comprised of the following: a cylindrical rotating vacuum anvil; a rotating knife roll; and a transfer device. In typical applications, a tape web is fed at a relatively low speed along the vacuum face of the rotating anvil, which is moving at a relatively higher surface speed and upon which the tape web is allowed to "slip." A knife-edge, mounted on the rotating knife roll, cuts a segment of tape from the tape web against the anvil face. This knife-edge is preferably moving at a surface velocity similar to that of the anvil's circumference. Once cut, the tape tab is held by vacuum drawn through holes on the anvil's face as it is carried at the anvil's speed downstream to the transfer point where the tape segment is transferred to the traveling web.

Continual improvements and competitive pressures have incrementally increased the operational speeds of disposable diaper converters. As speeds increased, the mechanical integrity and operational capabilities of the applicators had to be improved accordingly. As a further complication, the complexity of the tape tabs being attached has also increased. That is, for a given tape web design, cut tape tabs may need to be applied to a traveling web of material at a transfer position while the tape tabs are provided to the transfer position in a path that is skew to the travel direction of the web of material. Consumer product manufacturers offer tapes which are die-cut to complex profiles and which may be constructed of materials incompatible with existing applicators. For instance, a proposed tape tab may be a die-profiled elastic textile, instead of a typical straight-cut stiff-paper and plastic type used in the past. Consequently, a manufacturer may find itself with a window-knife applicator, which cannot feed a tape web with too little axial stiffness. It could also find itself with a slip-and-cut applicator, which cannot successfully apply die-cut tape segments. Furthermore, existing applicators cannot successfully apply tapes whose boundaries are fully profiled, as may be desired to eliminate sharp corners, which might irritate a baby's delicate skin. This demonstrates a clear need for an improved applicator capable of applying new tape configurations and overcoming other shortcomings of some prior art applicators.

To overcome some shortcomings, Parish et al. (U.S. Pat. No. 6,475,325), which has been assigned to the same assignee as the present application, discloses an applicator and method that allows tape tabs to be applied to a running web of material, even when the web of tape tab material is moving at a different speed than the web of material. A protuberance acting against the web of material brings the web into contact with the tape tabs and adheres the tape tabs to the web. While this invention adequately solved many of the problems of the prior art, it did not address the placement of tape tabs which are being fed in a direction that is skew to the traveling direction of the web of material.

SUMMARY OF THE INVENTION

The present invention has the added capability over the prior art by providing a method and apparatus for applying tabs to a traveling web of material at a transfer position when the tabs are provided to the transfer position in a path that is skew to the travel direction of the web of material.

The invention provides the additional benefit of quiet operation compared to prior art equipment, which uses high speed cutting faces and suffers from the effects of the very high energy levels seen at the point of contact. Generally, these energies, and the sounds that they generate, increase in proportion to the square of the velocity. The present invention benefits from the relatively low speed of the cutting faces and exhibits extremely low noise levels. In fact, the underlying noise of the mechanical drive systems and the traveling web equipment contribute to make the cutting noise level nearly unnoticeable.

The present invention provides a simplified process wherein a rotary knife or die, with one or more cutting edges, turns against and in coordination with a corresponding vacuum anvil cylinder. An infeeding tape web is fed along the surface of the anvil, which is rotating at a surface velocity equal to or only somewhat greater than that of the tape web. As the tape web passes the nip created between the knife-edges and the anvil surface, segments of tape are parted to form tape tabs but not significantly displaced upon the anvil surface. The tape tabs continue downstream on the anvil surface, held securely by forces induced by a vacuum source directed to one or more holes provided for each segment in the anvil surface.

At a point downstream, a transfer position, along the surface of the anvil, the traveling web to which the segments are to be attached is brought into close proximity with the anvil and its tape tabs at a transfer location. At the transfer position, the traveling web is proceeding in a direction that is skew to the tangent of the rotational direction of the anvil. A device, which may be as simple as a protuberance or multiple protuberances on a rotating cylinder, presses a target zone of the traveling web against an exposed adhesive of the tape tab as it is presented by the anvil surface. The protuberance preferably has a surface velocity substantially identical to that of the traveling web.

The present invention may include a vacuum commutation system configured to remove or reduce the level of vacuum used to hold each tab to the anvil surface just before the point of transfer. The materials and finishes selected for the anvil and the bump transfer surfaces provide a situation in which the coefficient of friction between the bump transfer surfaces and the traveling web is relatively high, while the coefficient of friction between the tape tab and the anvil is relatively low. The highly aggressive nature of the bond between the adhesive side of the tape tab and the target surface of the traveling web ensures that there is virtually no slippage between the two. This ensures that the traveling web is driven through the point of transfer at its existing velocity, and that any tendency of the tape tab to adhere to the anvil surface will not influence the traveling web. While some slippage may be inevitable, the slip occurs preferably only between the tape tab and the anvil surface. Given the extremely low moment of inertia of a tape tab and the aggressive adhesion provided between it and the compatible surface of the traveling web, each successive tape tab is successfully transferred to the traveling web, accelerating quickly to the speed of the traveling web.

The present invention allows for placement of tape onto areas of the disposable garment when the tape tabs are presented to the web at skew angles. For instance, training pants for babies typically have a removable panel in the rear of the diaper. A soiled panel is removed from the pants and rolled up and secured with the fastening tapes. The present invention provides for a method to apply the transverse fastening tapes to a diaper. Likewise, the present invention provides a method to attach tapes to sides of garments that are manufactured according to a transverse process.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1A:
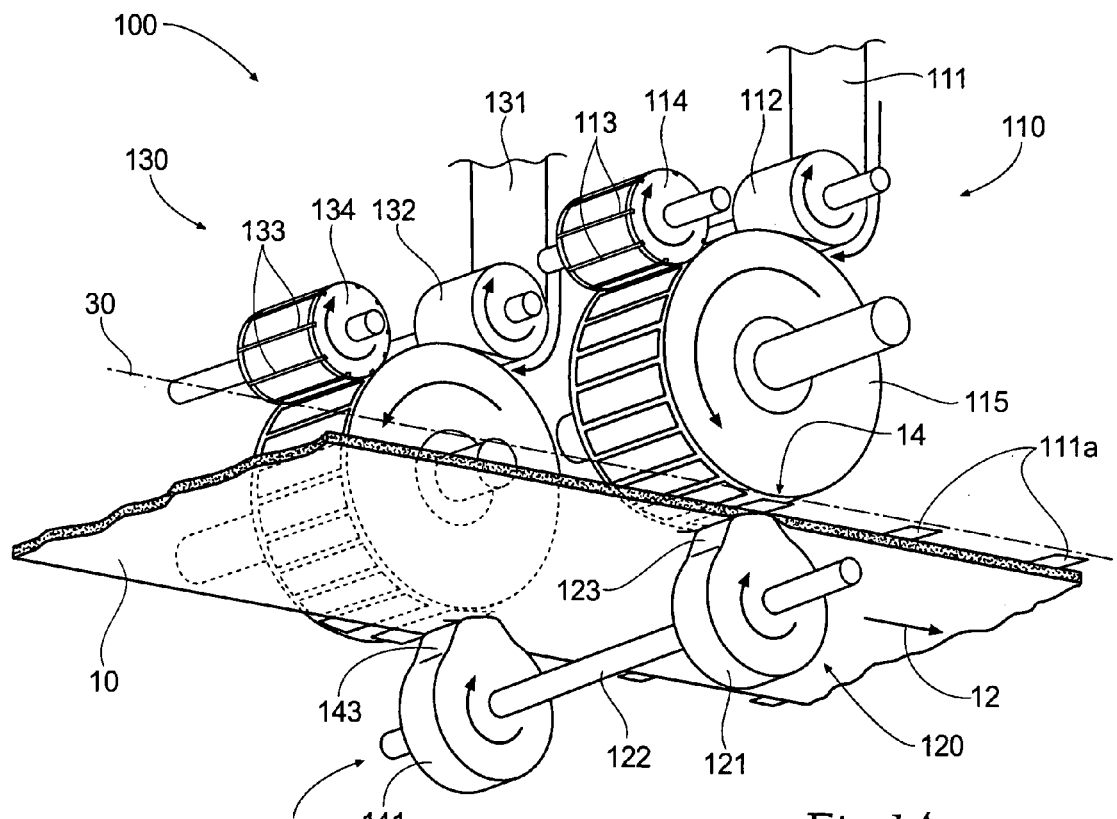
FIG. 1A is a perspective view of a prior art tape application apparatus.

FIG. 1A displays a perspective view of a prior art tape tab application apparatus 100, as disclosed in Parish et al. (U.S. Pat. No. 6,475,325), which has been assigned to the same assignee as the present application. The apparatus 100 includes a first tab supply assembly 110 and a first tab applicator 120, and it may further include a second tab supply assembly 130, and a second tab applicator 140. The first tab supply assembly 110 comprises a supplied web 111, which may be adhesive-coated, provided over a first roller 112 and through a nip created by at least one blade 113 disposed on a first rotary cutter 114 cooperating with a first anvil 115. The first anvil 115 includes a vacuum drawn through its circumferential surface to maintain tabs 111a in place from the time of cutting to a transfer location 14. At the transfer location 14 of this prior art apparatus 100, a tangent 30 of the anvil surface is parallel to the traveling direction 12 of the web 10. The first tab applicator 120 comprises a wheel 121 affixed to a rotatable shaft 122, the wheel 121 having a simple protuberance 123 formed thereon.

The web 111 is fed over the roller 112 onto the anvil 115. The web 111 is fed to the anvil 115 at a speed that approximately equals the speed at which the outer periphery of the anvil 115 is traveling. If desired, the anvil 115 may rotate at a slightly higher speed than the linear speed of the tape web 111. The at least one blade 113 of the rotary cutter 114 also travels at a peripheral speed substantially equal to that of anvil 115. After being cut, the tabs 111a are carried on the outer surface of the anvil 115. The tabs 111a are held in place by the vacuum provided from within the interior of the anvil 115. If the web 111 is coated with an adhesive, the adhesive-coated surface preferably faces outwardly while a preferably non-tacky surface engages the anvil 115.

The first tab applicator 120 engages the web 10 at a predetermined interval against a tab 111a located on the anvil 115 at the transfer position 14. The protrusion 123 serves to deflect a portion of the web 10 toward the anvil 115 in order to transfer the tab 111a onto the web 10.

The arrangement of the second tab supply assembly 130 and the second tab applicator 140 of this prior art apparatus 100 is similar to that of the first. The second tab supply assembly 130 comprises a supplied adhesive-coated tape web 131 provided over a roller 132 and through a nip created by at least one blade 133 disposed on a second rotary cutter 134 cooperating with a second anvil 135. The second anvil 135 includes a vacuum drawn through its circumferential surface to maintain tabs 131a in place from the time of cutting to a transfer location 14. The second tab applicator 140 comprises a wheel 141 affixed to the rotatable shaft 122, the wheel 141 having a simple protuberance 143 formed thereon.

The adhesive-coated tape web 131 is fed over the roller 132 onto the anvil 135. The tape web 131 is fed to the anvil 135 at a speed that approximately equals the speed at which the outer periphery of the anvil 135 is traveling. If desired, the anvil 135 may rotate at a slightly higher speed than the linear speed of the tape web 131. Blades 133 of the rotary cutter 134 also travel at a peripheral speed substantially equal to that of anvil 135. After being cut, the tabs 131a are carried on the outer surface of anvil 135. The tabs 131a are held in place by the vacuum provided from within the interior of the anvil 135. The adhesive-coated surface of the tape web 131 is facing outwardly while a preferably non-tacky surface engages the anvil 135.

The second tab applicator 140 engages the web 10 at a predetermined interval against a tab 131a located on the anvil 135 at the transfer position. The protrusion 143 serves to deflect a portion of the web 10 toward the anvil 135 in order to transfer the tab 131a onto the web 10.

Figure 1B:
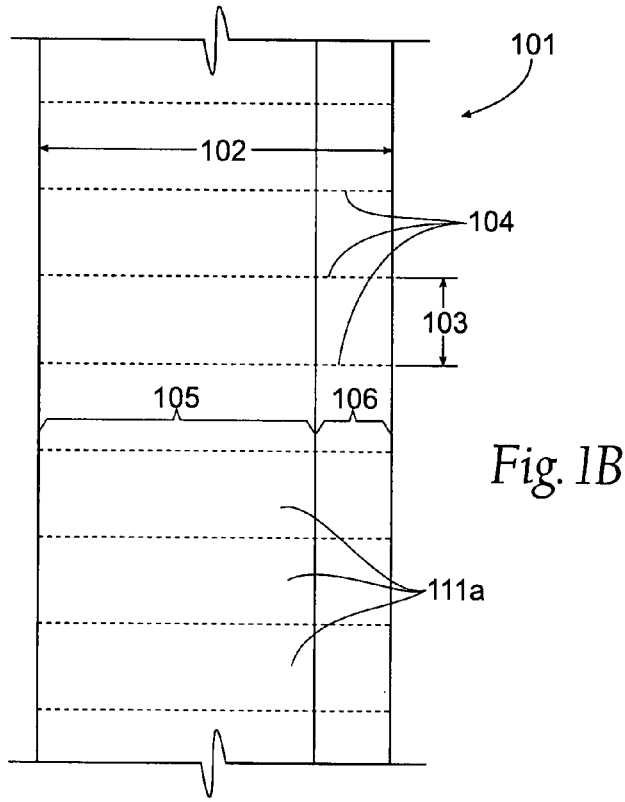
FIG. 1B is a top plan view of a tape to be applied by the prior art tape application apparatus of FIG. 1A.

FIG. 1B shows a top plan view of a tape web 101 to be cut into tape tabs 111a and applied to a traveling web 10. The tape web 101 has a tape web width 102 and the tape tabs 111a have a tape tab height 103. The web 101 is cut at various points 104 depending upon desired dimensions for the resulting tabs 111a. Each tab 111a has a first portion 105 and a second portion 106. The first portion 105 is preferably coated with an adhesive, while the second portion 106 may be provided with a hook-and-loop type, or other, fastening means.

Figure 1C:
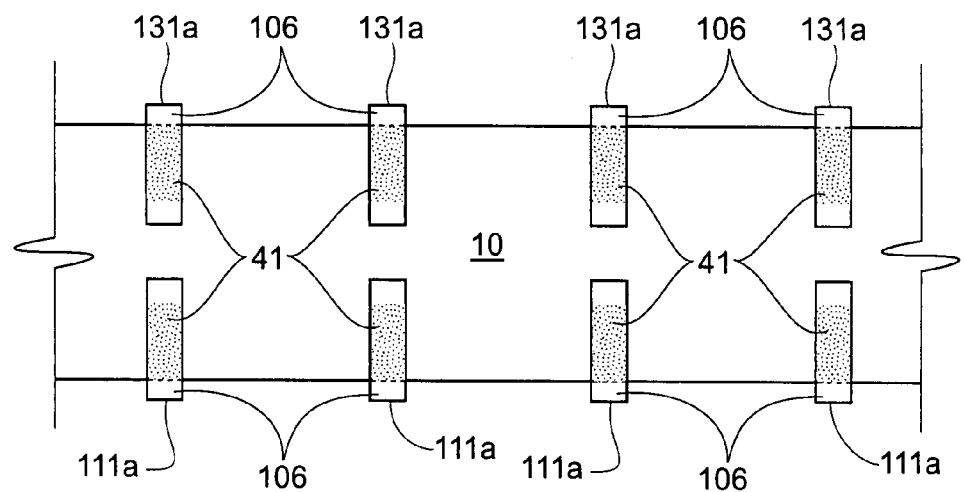
FIG. 1C is an overhead diagrammatic view of tape tabs cut from the tape of FIG. 1B applied by the prior art apparatus of FIG. 1A.

FIG. 1C shows an overhead view of a web of material 10 having tape tabs 111a applied to the web 10 by the prior art apparatus of FIG. 1A. The design of the tape web 111 and desirable tape tabs 111a allow a discrete protuberance 123 of the prior art apparatus 100 to create a sufficient attachment site 41 to maintain the tape tab 111a in positive adhesive contact with the web 10.

Figure 2A:
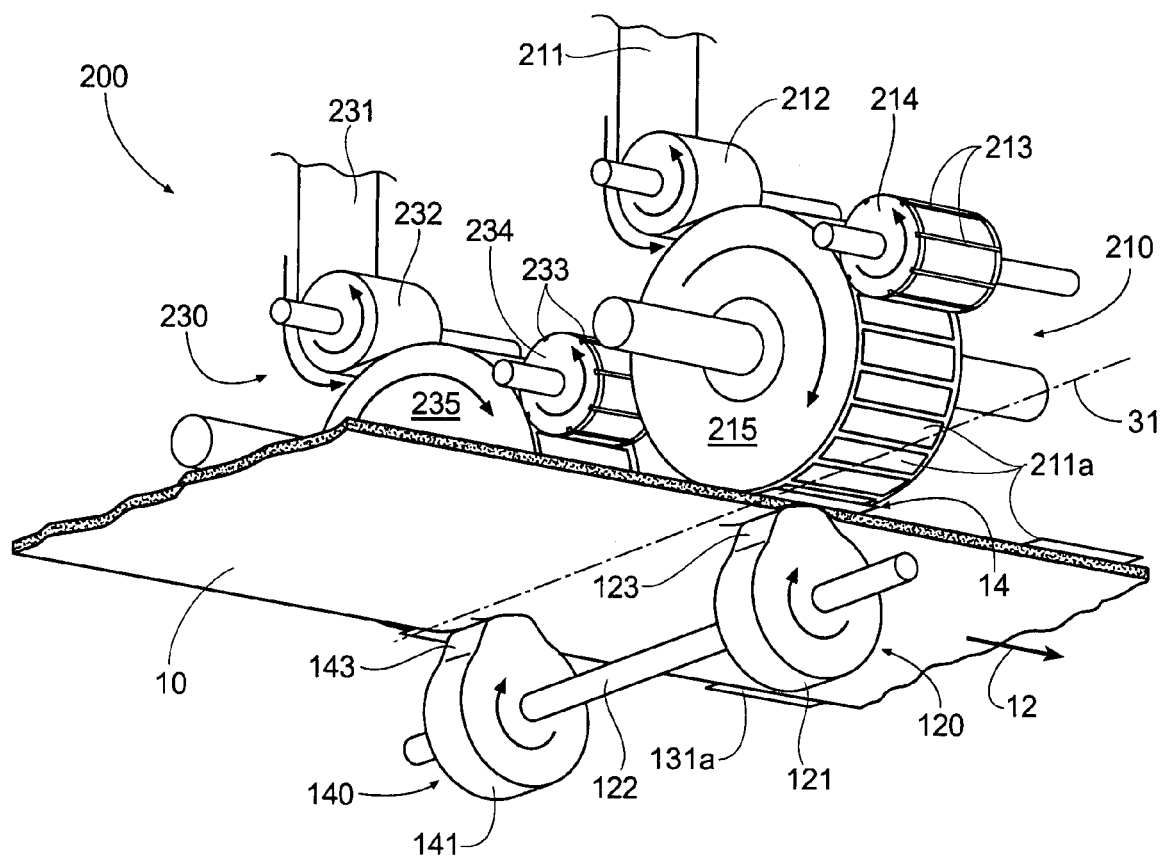
FIG. 2A is a perspective view of a transverse tab applicator disclosed in the priority application.

While the previous apparatus 100 provides generally sufficient operation for the specified tab configuration, other tab configurations may not be accommodated by the setup. FIG. 2A is a perspective view of an embodiment of a transverse tape tab applicator disclosed in the application to which priority is claimed. Like the prior art embodiment of FIG. 1A, this embodiment 200 includes tab supply assemblies 210,230 and the same tab applicators 120,140. It will be noted, however, that the tab supply assemblies 210,230 have been rotated ninety degrees so that a tangent 31 of the surface of either anvil 215,235 is not parallel to the traveling direction 12 of the web 10. Rather, at the transfer location 14, the tangent 31 of the anvil surfaces is substantially perpendicular skew to the traveling direction 12 of the web 10. As used herein, skew describes referenced structures or illustrative references that are perpendicular or oblique to one another, but are not coplanar.

Figure 2B:
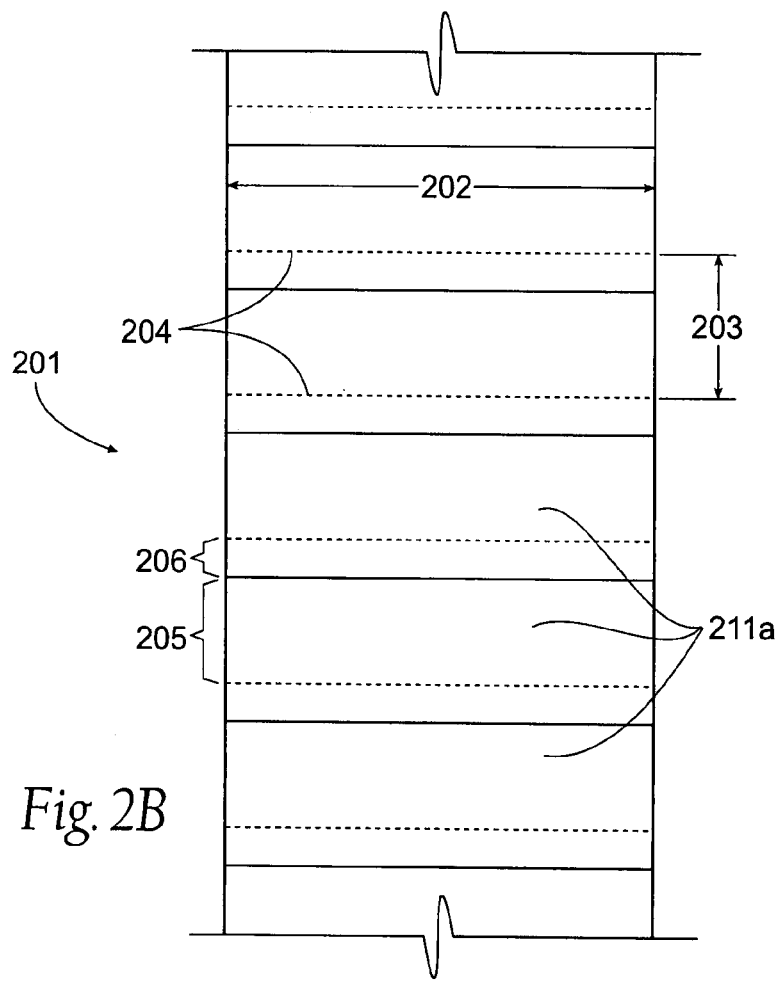
FIG. 2B is a top plan view of a web to be applied by the tab applicator of FIG. 2A.

FIG. 2B shows a top plan view of a web 201 to be cut into tabs 211a and applied to a traveling web 10. The web 201 has a web width 202 and the tabs 211a have a tab height 203. The web 201 is cut at various points 204 depending upon desired dimensions for the resulting tabs 211a. Each tab 211a has a first portion 205 and a second portion 206. The first portion 205 is preferably coated with an adhesive, while the second portion 206 may be provided with a hook-and-loop type fastening means. It should be noted that due to the respective orientation of the first portion 205 and the second portion 206, and the desired orientation on the web 10, the tabs 211a must be presented for affixation at an angle that is not parallel to the traveling direction 12 of the web 10, without major modifications to the tab supply assemblies 210,230.

Figure 2C:
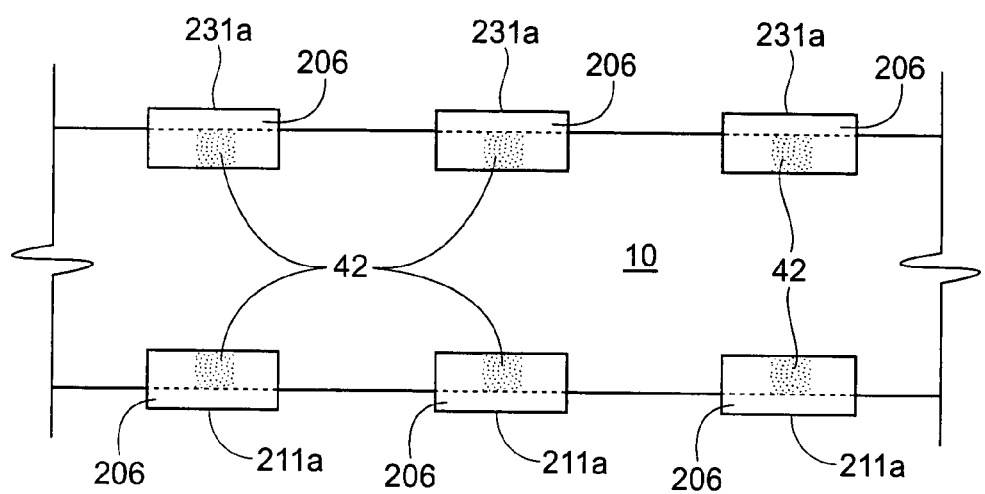
FIG. 2C is an overhead diagrammatic view of tabs cut from the web of FIG. 2B applied by the prior applicator of FIG. 2A.

FIG. 2C depicts tabs 211a, 231a placed on a web 10 by the embodiment 200 of a transverse tape tab applicator apparatus shown in FIG. 2A. However, despite the use of the same tape tab applicators 120,140 as the prior art embodiment 100, the orientation of the tape tabs 211a prevents the discrete protuberance 123 of this embodiment 200 from creating a sufficient attachment site 42 to maintain the tape tab 211a in positive adhesive contact with the web 10. That is, the relative dimensions of the tape tab 211a and the protuberance 123 provide the insufficient attachment site 42.

Figure 3A:
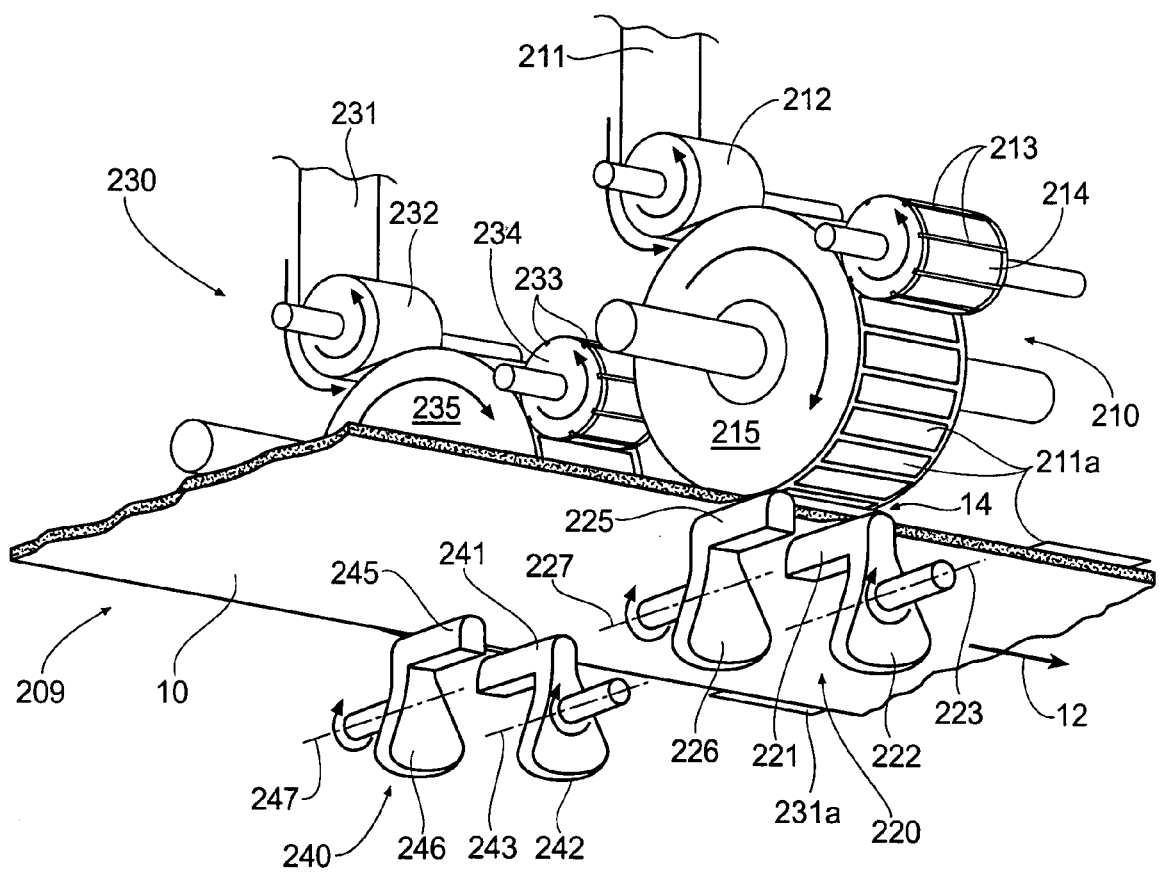
FIG. 3A is a perspective view illustrating an embodiment of the present invention.

In FIG. 3A there is shown a perspective view of an embodiment 209 of the present invention. Much like the apparatus in FIG. 2A, this embodiment 209 of the present invention provides a tab supply assembly 210. This embodiment 209, however, provides an improved tab applicator 220. optionally, the embodiment 209 may include a second tab supply assembly 230 and second tab applicator 240. While the tab applicators 220,240 are shown to be the same, identity is not required by the present invention. Indeed, detailed description of only one tab applicator 220 is provided, but if two applicators are used, it is preferable that the second applicator 240 be similar to the first 220. The tab applicator 220 of this embodiment 209 provides improved adhesion between a tab 211a and a traveling web 10. The applicator 220 includes a first bump transfer surface 221, which in conjunction with a first counterweight 222, is rotatable about an axis 223 and a second bump transfer surface 225, which in conjunction with a second counterweight 226, is rotatable about a second axis 227. Each bump transfer surface applies pressure to the web 10 preferably substantially simultaneously to the other. While such timing may be enabled in a variety of ways, the bump transfer surfaces 221,225 preferably travel in eccentric paths of revolution.

Figure 3B:
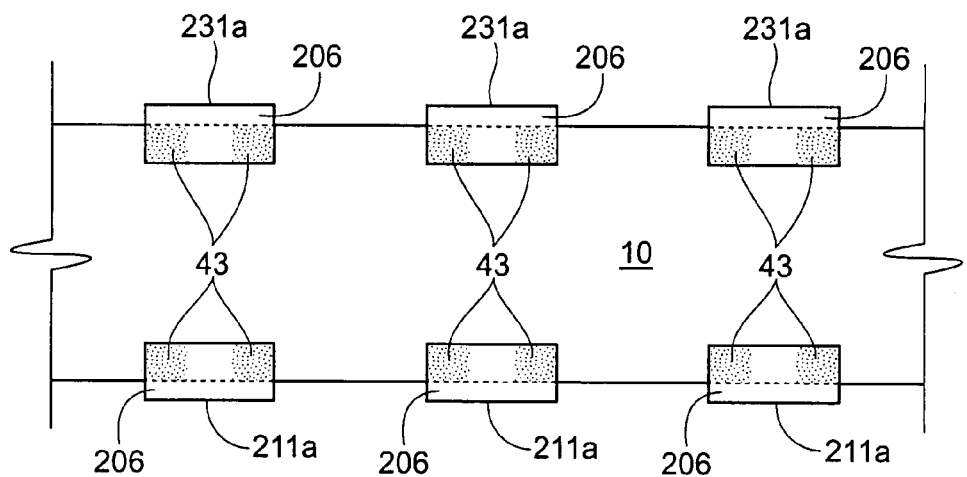
FIG. 3B is an overhead diagrammatic view of tabs cut from the web of FIG. 2B applied by the embodiment of FIG. 3A.

FIG. 3B is an overhead view of a web 10 having tabs 211a placed by the embodiment 209 of the apparatus and method of the present invention. As can be seen, the use of a modified tab applicator 220 provides a plurality of attachment sites 43 spaced at predetermined locations along the tab 211a, thereby improving adhesion between the tab 211a and the web 10.

Figure 4:
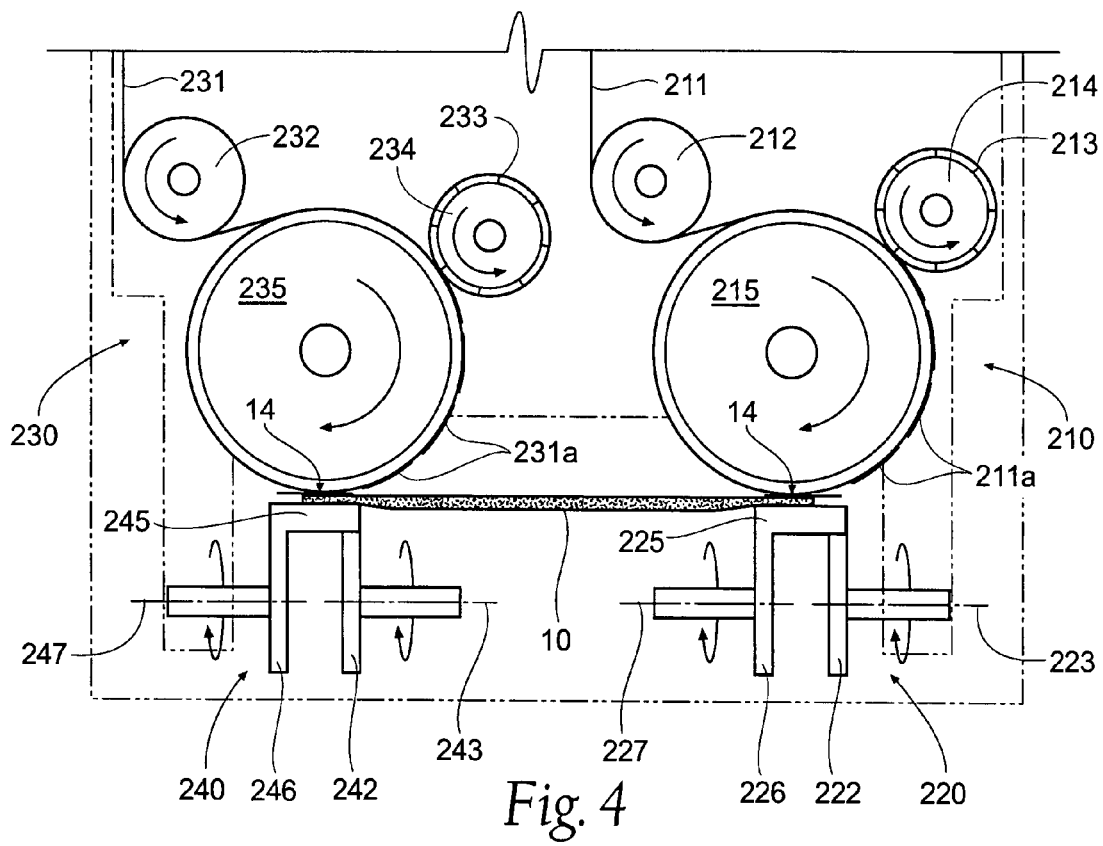
FIG. 4 is a front elevational view of the embodiment of FIG. 3A.

FIG. 4 shows a front elevation view of the apparatus of FIG. 3A. The incoming web 211 is fed about a roller 212. The web 211 travels further to contact the anvil 215. The web 211 is fed to the anvil 215 at a speed that approximately equals the speed at which the outer periphery of the anvil 215 is traveling. If desired, the anvil 215 may rotate at a slightly higher speed than the linear speed of the web 211. The blades 213 of the rotary cutter 214 are also traveling at a peripheral speed substantially equal to that of the anvil 215. After being cut, the tabs 211a are carried on the outer surface of the anvil 211a. The tabs 211a are held in place by vacuum provided within the interior of the anvil 215. If the web 211 is provided with an adhesive, the adhesive-coated surface preferably faces away from the anvil 215 while a non-tacky or uncoated surface preferably engages the exterior of the anvil 215.

The web 10 of diaper material is caused to travel in a path slightly displaced from the outer surface of the rotating anvil 215, but in close proximity thereto. Just below the web 10 is the tab applicator 220, whose bump transfer surfaces 221,225 rotate about their respective axes 223,227 at a peripheral velocity approximately equal to the lineal velocity of web 10, which, in turn, is usually substantially greater than the peripheral velocity of the anvil 215. Generally, once a tab 211a is at the transfer location 14, and the web 10 is in a desired position, the bump transfer surfaces 221,225 depress the web 10, causing the web 10 to come into contact with the anvil 215, thereby adhering the tab 211a to the web 10.

Figure 5A:
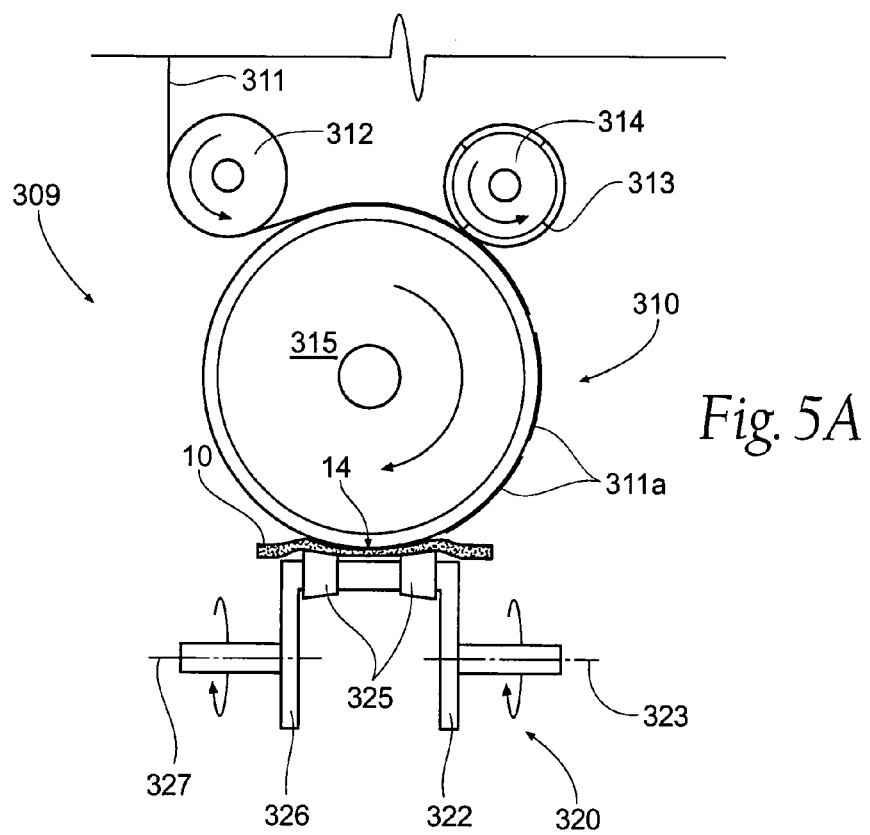
FIG. 5A is a front elevational view of a second embodiment of the invention.

A second embodiment 309 of the present invention is shown in FIG. 5A. While the first embodiment 209 is shown having a single bump transfer surface 221,225 on each transferor, each transferor may comprise a plurality of bump transfer surfaces 325, as shown in FIG. 5A. Likewise, the invention may be used with only one structure incorporating all transfer surfaces, instead of multiple structures. If two tab supply assemblies are used, the anvils 215 and 235 may rotate in the same direction, as shown, or it is possible to arrange them so that they are rotating in dissimilar directions if preferred, thereby allowing different orientations of the tabs.

Figure 5B:
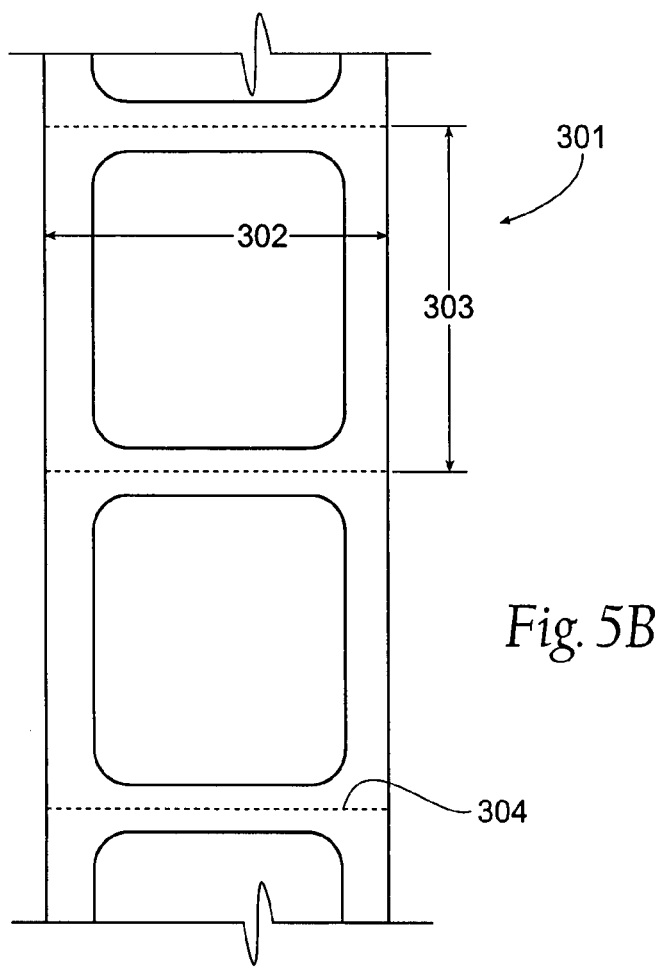
FIG. 5B is a top plan view of a web to be applied by the tab applicator of FIG. 5A.

FIG. 5B shows a top plan view of a web 301 to be cut into tabs 311a and applied to a traveling web 10. The web 301 has a web width 302 and the tabs 311a have a tab height 303. The web 301 is cut at various points 304 depending upon desired dimensions for the resulting tabs 311a.

Figure 5C:
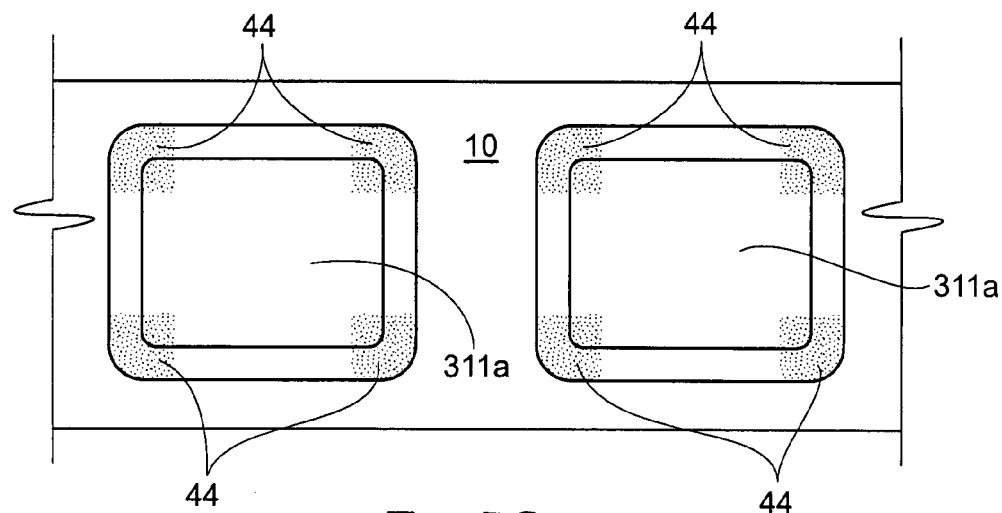
FIG. 5C is an overhead diagrammatic view of tabs cut from the web of FIG. 5B applied by the embodiment of FIG. 5A.

FIG. 5C shows an overhead view of a web of material 10 having tabs 311a applied to the web 10 by the embodiment 309 of FIG. 5A. As can be seen, the use of a modified tab applicator 320 provides a plurality of attachment sites 44 spaced at predetermined locations about the tab 311a, thereby improving adhesion between the tab 311a and the web 10.

Figure 6:
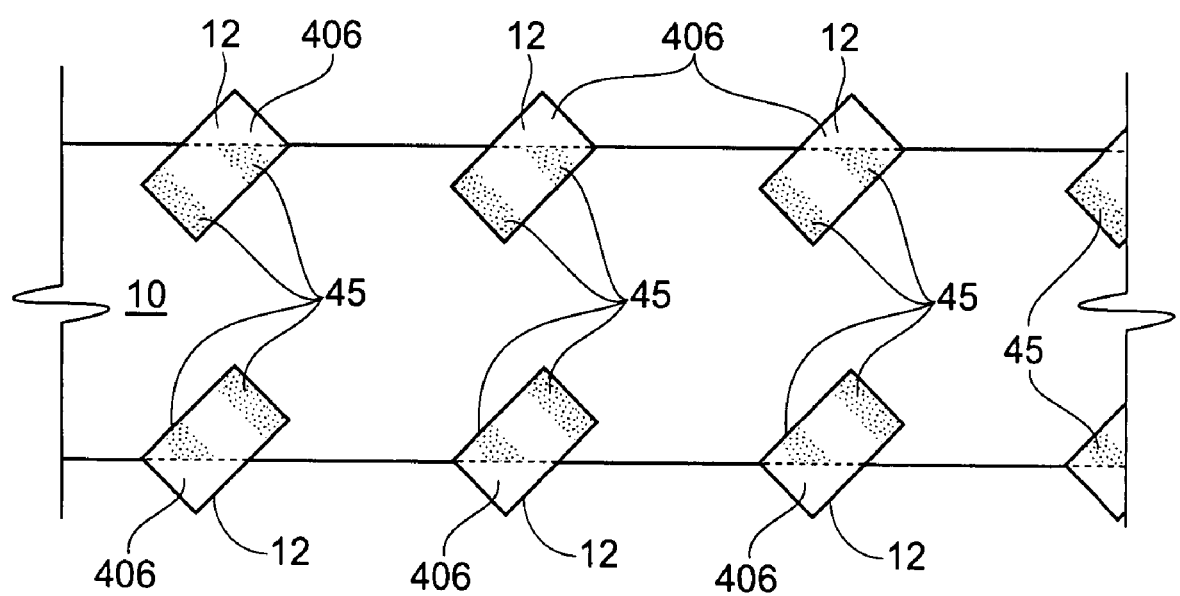
FIG. 6 is an overhead diagrammatic view of a second tab application according to the present invention.

As shown in FIG. 3A, FIG. 4, and FIG. 5A, the axes of rotation of the tab applicators 220,240 may be generally perpendicular skew from the axes of rotation of the anvils; however, the invention also contemplates tabs placed onto a web at a predetermined oblique skew angle. FIG. 6 represents a diagrammatic view of such an arrangement. The tabs 12 are provided to the transfer location 14 in an oblique skew manner and placed onto the web of material 10 at a desired angle, such as approximately a 45 degree angle. Therefore, the relative angle between the anvil surface tangent and the web 10 may lie at any skew angle, perpendicular or oblique.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. A method comprising the steps of:
   providing a plurality of tabs to a transfer position, the tabs traveling in a tab path;
   providing a web for receiving said tabs, said web traveling in a web path, the web path being skew to the tab path at the transfer position; and
   coupling said one of said tabs to said web by urging a plurality of protuberances intermittently against said target web to urge said web into contact with a single tab.

2. The method of claim 1, wherein the tab path is curved at the transfer position.

3. The method of claim 2, wherein the skew of the web path is substantially perpendicular to the tangent of the tab path at the transfer position.

4. A method comprising the steps of:
   providing a plurality of tabs to a transfer position, the tabs traveling in a tab path;
   providing a web for receiving said tabs, said web traveling in a web path, the web path being skew to the tab path at the transfer position; and
   coupling said one of said tabs to said web by urging a plurality of protuberances intermittently against said target web to urge said web into contact with a single tab;
   wherein the tab path is curved at the transfer position;
   wherein the skew of the web path is substantially perpendicular to the tangent of the tab path at the transfer position; and wherein the providing a tab step comprises rotating a drum carrying the tab.

5. The method of claim 1, wherein said tab is coupled to said traveling web by an adhesive.

6. The method of claim 5, wherein said adhesive is carried by said tab.

7. The method of claim 1, wherein said plurality of protuberances is rotated about a protuberance path into contact with said web.

8. The method of claim 1, wherein said plurality of protuberances are each carried by a wheel.

9. The method of claim 7, wherein a tangent of said protuberance path at said transfer position is substantially parallel with said web path.

10. A method comprising the steps of:
    rotating a drum carrying a tab to a transfer position, the rotation establishing a rotational path;
    providing a target web for receiving said tab, said target web traveling in a web direction, the web direction being oblique skew to a tangent of said rotational path at the transfer position; and
    coupling said tab to said web by intermittently urging a plurality of protuberances against said target web to urge said target web into contact with said tab, said tab being acted upon by at least two of said plurality of protuberances, said at least two of said plurality of protuberances acting upon said tab substantially simultaneously.

11. The method of claim 10, wherein said tab is coupled to said target web by an adhesive.

12. The method of claim 11, wherein said adhesive is carried by said tab.

13. The method of claim 10, wherein at least one of the plurality of protuberances is rotated into contact with said target web.

14. The method of claim 10, wherein said plurality of protuberances are carried by a wheel.

15. The method of claim 10, wherein said plurality of protuberances are rotated substantially parallel with said web path.

* * * * *